US007910721B2

(12) United States Patent
Katahira

(10) Patent No.: US 7,910,721 B2
(45) Date of Patent: Mar. 22, 2011

(54) NUCLEIC ACID-ENZYME COMPLEX

(75) Inventor: Masato Katahira, Yokohama (JP)

(73) Assignee: National University Corporation Yokohama National University, Kanagawa (JP)

(*) Notice: Subject to any disclaimer, the term of this patent is extended or adjusted under 35 U.S.C. 154(b) by 1145 days.

(21) Appl. No.: 11/596,057

(22) PCT Filed: Apr. 18, 2005

(86) PCT No.: PCT/JP2005/007378
§ 371 (c)(1),
(2), (4) Date: Nov. 9, 2006

(87) PCT Pub. No.: WO2005/108570
PCT Pub. Date: Nov. 17, 2005

(65) Prior Publication Data
US 2009/0081756 A1  Mar. 26, 2009

(30) Foreign Application Priority Data

May 11, 2004  (JP) ................................. 2004-141327

(51) Int. Cl.
*C07H 21/04* (2006.01)
*C07H 21/02* (2006.01)
*A61K 48/00* (2006.01)
*A61K 35/00* (2006.01)

(52) U.S. Cl. ........ 536/24.5; 536/23.1; 514/44; 424/93.1

(58) Field of Classification Search .................. None
See application file for complete search history.

(56) References Cited

FOREIGN PATENT DOCUMENTS

| JP | 7-231784 | 9/1995 |
|---|---|---|
| JP | 10-509039 | 9/1998 |
| JP | 2003-265168 | 9/2003 |
| WO | 96/15240 | 5/1996 |
| WO | WO 01/96559 | 12/2001 |

OTHER PUBLICATIONS

Supplementary European Search Report corresponding to European Patent Application No. 05730493.3-2401 dated Oct. 19, 2007.
Search Report dated Aug. 16, 2005 for International Application No. PCT/JP2005/007378 filed Apr. 18, 2005. (translated).
Jim Haseloff et al., "Simple RNA Enzymes with New and Highly Specific Endoribonuclease Activites", Nature, Aug. 18, 1988, pp. 585-591, vol. 334, Nature Publishing Group, London, England.
Akimasa Matsugami et al., "An Intramolecular Quadruplex of (GGA)$_4$ Triplet Repeat DNA with a G:G:G:G Tetrad and a G(:A):G(:A):G(:A):G Heptad, and its Dimeric Interaction", J. Mol. Biol., 2001, pp. 255-269, vol. 313, Academic Press, London, England.
Akimasa Matsugami et al., "Intramolecular Higher Order Packing of Parallel Quadruplexes Comprising a G:G:G:G Tetrad and a G(:A):G(:A): G(:A):G Heptad of GGA Triplet Repeat DNA", Jul. 18, 2003, pp. 28147-28153, vol. 278, No. 30, American Society for Biochemistry and Molecular Biology, Baltimore, Maryland.
Stephen W. Santoro et al., "A General Purpose RNA-Cleaving DNA Enzyme", Proceedings of the National Academy of Sciences USA, Apr. 1997, pp. 4262-4266, vol. 94, Proceedings of the National Academy of Sciences USA.
Żaneta Zaborowska et al., "Sequence Requirments in the Catalytic Core of the "10-23" DNA Enzyme", The Journal of Biological Chemistry, Oct. 25, 2002, pp. 40617-40622, vol. 277, No. 43, American Society for Biochemistry and Molecular Biology, Baltimore, Maryland.
Naoki Sugimoto et al., "Effect of Metal Ions and Sequence of Deoxyribozymes on their RNA Cleavage Activity", Perkins Trans. 2, 1999, pp. 1381-1386, Journal of the Chemical Society, London, England.
Alessio Peracchi, "Preferential Activation of the 8-17 Deoxyribozyme by $Ca^{2+}$ Ions", The Journal of Biological Chemistry, Apr. 21, 2000, pp. 11693-11697, vol. 275, No. 16, American Society for Biochemistry and Molecular Biology, Baltimore, Maryland.
Anat R. Feldman et al., "A New and Efficient DNA Enzyme for the Sequence-Specific Cleavage of RNA", Journal of Molecular Biology, 2001, pp. 283-294, vol. 313, Academic Press, London, England.
Adam Roth et al., "An Amino Acid as a Cofactor for a Catalytic Polynucleotide", Proceedings of the National Academy of Sciences USA, May 1998, pp. 6027-6031, vol. 95, National Academy of Sciences, Washington, DC.
Nir Carmi et al., "Cleaving DNA with DNA", Proceedings of the National Academy of Sciences USA, Mar. 1998, pp. 2233-2237, vol. 95, National Academy of Sciences, Washington, DC.
Stephen W. Santoro et al., "RNA Cleavage by a DNA Enzyme with Extended Chemical Functionality", Journal of the American Chemical Society, 2000, pp. 2433-2439, vol. 122, American Chemical Society, Easton, Pennsylvania.
Stephen W. Santoro et al., "Mechanism and Utility of an RNA-Cleaving DNA Enzyme", Biochemistry, 1998, pp. 13330-13342, vol. 37, American Chemical Society, Washington, DC.
Tetsuya Toyoda et al., "Inhibition of Influenza Virus Replication in Cultured Cells by RNA-Cleaving DNA Enzyme", FEBS Letters, 2000, pp. 113-116, vol. 481, Elsevier Science BV, Amsterdam, Holland.

(Continued)

*Primary Examiner* — Amy Bowman
(74) *Attorney, Agent, or Firm* — Jenkins, Wilson, Taylor & Hunt, P.A.

(57) ABSTRACT

The present invention provides a method for controlling cleavage of a target RNA by deoxyribozyme.

The present inventors designed a nucleic acid-enzyme complex using GGA 12-mer (Reference 3), which was found in the laboratory of the inventors to have greatly changeable structure in the presence or absence of monovalent metal ion as well as previously known nucleic acid-enzyme. The present invention is a deoxyribozyme complex comprising deoxyribozyme having a nucleotide sequence of target RNA, a substrate binding domain and a catalytic domain of RNA cleavage reaction, and a sequence (5'GGAGGAGGAGGA3' (SEQ ID NO: 21)), wherein the sequence is inserted to the catalytic domain of RNA cleavage reaction.

9 Claims, 5 Drawing Sheets

OTHER PUBLICATIONS

Hiroshi Sugiyama et al., "Catalytic Activities of Hammerhead Ribozymes with a Triterpenoid Linker Instead of Stem/Loop II", FEBS Letters, 1996, vol. 392, No. 3, pp. 215-219, Elsevier Science BV, Amsterdam, Holland.

Philip Hendry et al., "Using Linkers to Investigate the Spatial Separation of the Conserved Nucleotides $A_9$ and $G_{12}$ in the Hammerhead Ribozyme", Biochimica et Biophysica Acta, 1994, pp. 405-412, vol. 1219, No. 2, Elsevier, Amsterdam, Holland.

Narendra K. Vaish et al., "In Vitro Selection of a Purine Nucleotide-Specific Hammerhead-like Ribozyme", Proceedings of the National Academy of Sciences USA, Mar. 1998, pp. 2158-2162, vol. 95, No. 5, National Academy of Sciences, Washington, DC.

Laurent Bellon et al., "Post-Synthetically Ligated Ribozymes: An Alternative Approach to Iterative Solid-Phase Synthesis", Bioconjugate Chemistry, 1997, pp. 204-212, vol. 8, No. 2, American Chemical Society, Washington, DC.

(A) the structure of GGA 12-mer (B)  G:G:G:G tetrad (C)  G(:A):G(:A):G(:A):G heptad

SEQUENCE LISTING

```
<160> NUMBER OF SEQ ID NOS: 29

<210> SEQ ID NO 1
<211> LENGTH: 12
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (12)..(12)
<223> OTHER INFORMATION: n is a, c, g, or t

<400> SEQUENCE: 1
ggaggaggag gn                                                            12

<210> SEQ ID NO 2
<211> LENGTH: 17
<212> TYPE: RNA
<213> ORGANISM: Artificial Sequence
<220> FEATURE:
<223> OTHER INFORMATION: Artificially synthesized oligonucleotide

<400> SEQUENCE: 2
uauucaauau ggaaaga                                                       17

<210> SEQ ID NO 3
<211> LENGTH: 43
<212> TYPE: DNA
<213> ORGANISM: Artificial Sequence
<220> FEATURE:
<223> OTHER INFORMATION: Artificially synthesized oligonucleotide

<400> SEQUENCE: 3
tctttccagg ctagctacgg aggaggagga aacgaattga ata                          43

<210> SEQ ID NO 4
<211> LENGTH: 31
<212> TYPE: DNA
<213> ORGANISM: Artificial Sequence
<220> FEATURE:
<223> OTHER INFORMATION: Artificially synthesized oligonucleotide

<400> SEQUENCE: 4
tctttccagg ctagctacaa cgaattgaat a                                       31
```

<210> SEQ ID NO 5
<211> LENGTH: 31
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(7)
<223> OTHER INFORMATION: n is a, c, g, or t

<400> SEQUENCE: 5
nnnnnnnrgg ctagctacaa cgacccccccc c                                    31

<210> SEQ ID NO 6
<211> LENGTH: 31
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (8)..(8)
<223> OTHER INFORMATION: r is g or a
<220> FEATURE:
<221> NAME/KEY: misc_feature
<222> LOCATION: (11)..(11)
<223> OTHER INFORMATION: m is a or c
<220> FEATURE:
<221> NAME/KEY: misc_feature
<222> LOCATION: (13)..(13)
<223> OTHER INFORMATION: m is a or c
<220> FEATURE:
<221> NAME/KEY: misc_feature
<222> LOCATION: (15)..(15)
<223> OTHER INFORMATION: h is a, c, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (17)..(17)
<223> OTHER INFORMATION: d is a, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (21)..(21)
<223> OTHER INFORMATION: m is a or c
<220> FEATURE:
<221> NAME/KEY: misc_feature
<222> LOCATION: (23)..(23)
<223> OTHER INFORMATION: d is a, g, or t
<220> FEATURE:
<221> NAME/KEY: misc_feature
<222> LOCATION: (24)..(31)
<223> OTHER INFORMATION: n is a, c, g, or t

<400> SEQUENCE: 6
nnnnnnnrgg mtmghndnnn mgdnnnnnnn n                                     31

<210> SEQ ID NO 7
<211> LENGTH: 27
<212> TYPE: DNA
<213> ORGANISM: Artificial Sequence
<220> FEATURE:
<223> OTHER INFORMATION: Artificially synthesized oligonucleotide
<220> FEATURE:

```
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (20)..(27)
<223> OTHER INFORMATION: n is a, c, g, or t

<400> SEQUENCE: 7
nnnnnnnrgg ctacaacgan nnnnnnn                                               27

<210> SEQ ID NO 8
<211> LENGTH: 27
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (21)..(27)
<223> OTHER INFORMATION: n is a, c, g, or t

<400> SEQUENCE: 8
nnnnnntccg agccggacga nnnnnnn                                               27

<210> SEQ ID NO 9
<211> LENGTH: 33
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (28)..(33)
<223> OTHER INFORMATION: n is a, c, g, or t

<400> SEQUENCE: 9
nnnnnnnagg aggtaggggt tccgctcnnn nnn                                        33

<210> SEQ ID NO 10
<211> LENGTH: 36
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(33)
<223> OTHER INFORMATION: n is a, c, g, or t

<400> SEQUENCE: 10
ctcttcagcg atccggaacg gcacccatgt tagtga                                     36

<210> SEQ ID NO 11
<211> LENGTH: 39
<212> TYPE: DNA
<213> ORGANISM: Artificial Sequence
<220> FEATURE:
<223> OTHER INFORMATION: Artificially synthesized oligonucleotide

<400> SEQUENCE: 11
catctcttaa cggggctgcg gctaggaagt aatagtgag                                  39
```

```
<210> SEQ ID NO 12
<211> LENGTH: 25
<212> TYPE: DNA
<213> ORGANISM: Artificial Sequence
<220> FEATURE:
<223> OTHER INFORMATION: Artificially synthesized oligonucleotide

<400> SEQUENCE: 12
tgagtctggg cctcttttta agaac                                           25

<210> SEQ ID NO 13
<211> LENGTH: 26
<212> TYPE: DNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n refers to imidazol modified deoxyuracil
<220> FEATURE:
<221> NAME/KEY: misc_feature
<222> LOCATION: (17)..(18)
<223> OTHER INFORMATION: n refers to imidazol modified deoxyuracil
<220> FEATURE:
<221> NAME/KEY: misc_feature
<222> LOCATION: (20)..(26)
<223> OTHER INFORMATION: n is a, c, g, or t

<400> SEQUENCE: 13
nnnnnnngnt gaccccnngn nnnnnn                                          26

<210> SEQ ID NO 14
<211> LENGTH: 39
<212> TYPE: RNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(8)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (17)..(26)
<223> OTHER INFORMATION: n is a, c, g, or u
<220> FEATURE:
<221> NAME/KEY: misc_feature
<222> LOCATION: (32)..(39)
<223> OTHER INFORMATION: n is a, c, g, or u

<400> SEQUENCE: 14
nnnnnnnncu gangagnnnn nnnnnncgaa annnnnnnn                            39

<210> SEQ ID NO 15
<211> LENGTH: 31
<212> TYPE: RNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(8)
<223> OTHER INFORMATION: n is a, c, g, or u
<220> FEATURE:
```

```
<221> NAME/KEY: misc_feature
<222> LOCATION: (24)..(31)
<223> OTHER INFORMATION: n is a, c, g, or u

<400> SEQUENCE: 15
nnnnnnnncu gaugauuuug aaannnnnnn n                                        31

<210> SEQ ID NO 16
<211> LENGTH: 50
<212> TYPE: RNA
<213> ORGANISM: Artificial Sequence
<220> FEATURE:
<223> OTHER INFORMATION: Artificially synthesized oligonucleotide
<220> FEATURE:
<221> NAME/KEY: misc_feature
<222> LOCATION: (1)..(6)
<223> OTHER INFORMATION: n is a, c, g, or u
<220> FEATURE:
<221> NAME/KEY: misc_feature
<222> LOCATION: (11)..(14)
<223> OTHER INFORMATION: n is a, c, g, or u

<400> SEQUENCE: 16
nnnnnnagaa nnnnaccaga gaaacacacg uugugguaua uuaccuggua                    50

<210> SEQ ID NO 17
<211> LENGTH: 10
<212> TYPE: RNA
<213> ORGANISM: Artificial Sequence
<220> FEATURE:
<223> OTHER INFORMATION: Artificially synthesized oligonucleotide

<400> SEQUENCE: 17
cugggagucc                                                                10

<210> SEQ ID NO 18
<211> LENGTH: 74
<212> TYPE: RNA
<213> ORGANISM: Hepatitis D virus

<400> SEQUENCE: 18
gucccagccu ccucgcuggc gccggcuggg caacauuccg aggggaccgu ccccucggua         60
auggcgaaug ggac                                                           74

<210> SEQ ID NO 19
<211> LENGTH: 69
<212> TYPE: RNA
<213> ORGANISM: Artificial Sequence
<220> FEATURE:
<223> OTHER INFORMATION: Artificially synthesized oligonucleotide

<400> SEQUENCE: 19
cuccaccucc ucgcgguccg accugggcau ccgaaggagg ucgcacgacc acucggaugg         60
cuaagggag                                                                 69

<210> SEQ ID NO 20
<211> LENGTH: 52
<212> TYPE: RNA
<213> ORGANISM: Artificial Sequence
<220> FEATURE:
<223> OTHER INFORMATION: Artificially synthesized oligonucleotide

<400> SEQUENCE: 20
ggcccagccu ccucgcggcc cgaccugggc aucuucggau ggcgaauggg uc                 52

<210> SEQ ID NO 21
```

```
<211> LENGTH: 12
<212> TYPE: DNA
<213> ORGANISM: Artificial sequence
<220> FEATURE:
<223> OTHER INFORMATION: artificially synthesized oligonucleotide

<400> SEQUENCE: 21
ggaggaggag ga                                                              12

<210> SEQ ID NO 22
<211> LENGTH: 15
<212> TYPE: DNA
<213> ORGANISM: Artificial sequence
<220> FEATURE:
<223> OTHER INFORMATION: artificially synthesized oligonucleotide

<400> SEQUENCE: 22
tcactatagg aagag                                                           15

<210> SEQ ID NO 23
<211> LENGTH: 19
<212> TYPE: DNA
<213> ORGANISM: Artificial sequence
<220> FEATURE:
<223> OTHER INFORMATION: artificially synthesized oligonucleotide

<400> SEQUENCE: 23
ctcactatag gaagagatg                                                       19

<210> SEQ ID NO 24
<211> LENGTH: 18
<212> TYPE: DNA
<213> ORGANISM: Artificial sequence
<220> FEATURE:
<223> OTHER INFORMATION: artificially synthesized oligonucleotide

<400> SEQUENCE: 24
gaattctaat acgactca                                                        18

<210> SEQ ID NO 25
<211> LENGTH: 14
<212> TYPE: RNA
<213> ORGANISM: Artificial sequence
<220> FEATURE:
<223> OTHER INFORMATION: Artificially synthesized oligonucleotide
<220> FEATURE:
<221> NAME/KEY: misc_feature
<222> LOCATION: (1)..(3)
<223> OTHER INFORMATION: n is a, g, c, or u
<220> FEATURE:
<221> NAME/KEY: misc_feature
<222> LOCATION: (4)..(4)
<223> OTHER INFORMATION: b is g, c, or u
<220> FEATURE:
<221> NAME/KEY: misc_feature
<222> LOCATION: (5)..(5)
<223> OTHER INFORMATION: n is a, g, c, or u
<220> FEATURE:
<221> NAME/KEY: misc_feature
<222> LOCATION: (9)..(14)
<223> OTHER INFORMATION: n is a, g, c, or u

<400> SEQUENCE: 25
nnnbngucnn nnnn                                                            14

<210> SEQ ID NO 26
<211> LENGTH: 12
<212> TYPE: DNA
<213> ORGANISM: Artificial sequence
<220> FEATURE:
```

-continued

```
<223> OTHER INFORMATION: artificially synthesized oligonucleotide

<400> SEQUENCE: 26
ggaccgagcc ag                                                            12

<210> SEQ ID NO 27
<211> LENGTH: 11
<212> TYPE: DNA
<213> ORGANISM: Artificial sequence
<220> FEATURE:
<223> OTHER INFORMATION: Artificially synthesized oligonucleotide

<400> SEQUENCE: 27
ugauggccgg c                                                             11

<210> SEQ ID NO 28
<211> LENGTH: 12
<212> TYPE: DNA
<213> ORGANISM: Artificial sequence
<220> FEATURE:
<223> OTHER INFORMATION: Artificially synthesized oligonucleotide

<400> SEQUENCE: 28 ucuucgggguc gg                                                           12

<210> SEQ ID NO 29
<211> LENGTH: 8
<212> TYPE: DNA
<213> ORGANISM: Artificial sequence
<220> FEATURE:
<223> OTHER INFORMATION: Artificially synthesized oligonucleotide

<400> SEQUENCE: 29 cgggucgg                                                                  8
```

US 7,910,721 B2

NUCLEIC ACID-ENZYME COMPLEX

CROSS REFERENCE TO RELATED APPLICATIONS

This application is a National Stage of International Application No. PCT/JP2005/007378, filed Apr. 18, 2005, and which claims benefit of Japanese Patent Application No.: 2004-141327 filed May 11, 2004.

REFERENCE TO A SEQUENCE LISTING

A Sequence Listing containing SEQ ID NOS.: 1-22 is incorporated herein by reference.

FIELD OF THE INVENTION

The present invention relates to a nucleic acid-enzyme complex, which cleaves a target RNA and controls the cleavage, and a method for cleaving the target RNA using the complex under control.

PRIOR ART

RNA is an intermediate for translating genetic information into proteins. Furthermore, since the discovery of ribozyme (Nature vol. 334, 585-591, 1988), which is RNA having a catalytic activity, RNA attracts much attention due to the fact that RNA is repressible a specific gene expression.

Moreover, deoxyribozyme (DNA enzyme), which was found recently to have a catalytic activity, is superior to ribozyme in that the former is chemically more stable, easily prepared and treated than the latter. DNA enzyme with an activity to cleave a specific sequence of RNA might be used as a tool to cleave mRNA of deleterious genes.

These ribozyme and deoxyribozyme have been tried to apply to a cleavage agent of RNA, such as virus and pathogenic genes, or to a sensor tip (References 1 and 2).

While the present inventors performed structural analysis of d(GGAGGAGGAGGA) (SEQ ID NO: 21, an embodiment of SEQ ID NO: 1 wherein N of SEQ ID NO: 1 is A; where both SEQ ID NO: 21 and sometimes SEQ ID NO: 1 are also referred to hereinafter as "GGA 12-mer"), one of the triplet repeats which controls gene expression at transcriptional or translational level, using NMR, they found that the GGA-repeat DNA forms an intramolecular parallel quadruplex chain structure under physiological $K^+$ (intracellular $K^+$ concentrations around 140 mM) conditions (References 3 & 4).

Reference 1: Japanese Patent Application Public Disclosure (Kokai) H7-231784
Reference 2: Japanese Patent Application Public Disclosure (Kokai) 2003-265168
Reference 3: J. Mol. Biol. (2001) 313, 255-269
Reference 4: J. Biol. Chem. vol. 278, No. 30, 28147-28153, 2003

PROBLEMS TO BE SOLVED BY THE INVENTION

Previously, it was not possible for nucleic acid-enzyme to control the switching or the degree of the activity when cleaving RNA. Therefore, the target RNA could not be cleaved in a good timing and its application was limited.

The purpose of the present invention is to provide a means for controlling the cleavage of a target RNA by nucleic acid-enzyme.

MEANS TO SOLVE THE PROBLEMS

To resolve the problems, the present inventors designed a nucleic acid-enzyme complex using GGA 12-mer (Reference 3), which was found in the laboratory of the inventors to have changeable structure from single strand to quadruplex chain structure in the presence or absence of monovalent metal ion as well as previously known nucleic acid-enzyme (i.e. ribozyme and deoxyribozyme). More precisely, the present inventors constructed a nucleic acid-enzyme complex by cleaving a nucleic acid-enzyme into two subunits and by connecting the subunits with GGA 12-mer.

Since the two subunits of the nucleic acid-enzyme complex are separated due to failed formation of quadruplex chain structure of GGA 12-mer in the absence or in the low concentration of monovalent metal ion, the catalytic domain of the nucleic acid-enzyme is unable to form an active structure and no or weak cleavage activity is generated. However, the increase in the concentration of monovalent metal ion added in the reaction system changes the GGA 12-mer, which was previously present in the extended single strand, to a structure of compact quadruplex chain structure, allows the two separated subunits of the nucleic acid-enzyme to come close each other, and allows the complex to form an active structure and to generate strong cleavage activity.

The present invention enables to control the switching or the degree of the RNA cleavage activity of nucleic acid-enzyme by the regulation of the concentration of monovalent metal ion by the use of the nucleic acid-enzyme complex composed of nucleic acid-enzyme and GGA 12-mer.

In other words, the present invention is a nucleic acid-enzyme complex comprising a catalytic domain of RNA cleavage reaction and a substrate binding domain of a nucleic acid-enzyme (i.e. ribozyme and deoxyribozyme) and a sequence (5'GGAGGAGGAGGN3' (SEQ ID NO: 1)), wherein the substrate binding domain has a complementary relationship to the binding site of a target RNA and the sequence (5'GGAGGAGGAGGN3' (SEQ ID NO: 1)) or a sequence having a linker at least to one of both ends of the sequence is inserted in the catalytic domain of the RNA cleavage reaction. The nucleic acid-enzyme complex has preferably two substrate binding domains and the catalytic domain of RNA cleavage reaction is sandwiched by the two substrate binding domains.

Furthermore, the present invention is a method for controlling target RNA cleavage in a system comprising the nucleic acid-enzyme complex, an element essential for making the nucleic-acid enzyme active, a target RNA and a monovalent metal ion, wherein the nucleic-acid enzyme is the origin of the nucleic acid-enzyme complex, comprising the steps of keeping the concentration of the monovalent metal ion at more than or equal to 10 mmol/L and keeping the concentration of the monovalent metal ion at less than 10 mmol/L.

Moreover, the present invention is a method for cleaving an target RNA located in a cell comprising introducing the nucleic acid-enzyme complex into the cell.

Still furthermore, the present invention is a cell introduced the nucleic acid-enzyme complex.

EFFECTS OF THE INVENTION

The nucleic acid-enzyme complex of the present invention has higher catalytic activity, under the condition when the concentration of monovalent metal ion is more than a given concentration, than that, under when the concentration is less than a given concentration. Therefore, it is possible to control the switching ON/OFF or the degree of the RNA cleavage activity by regulating the concentration of the monovalent metal ion. Since the RNA cleavage site by the nucleic acid-enzyme complex is the same to that by DNA enzyme before subunit separation, it is interpreted that formation of quadruplex chain structure allows the subunits to come close to each other and to reconstruct an active structure of nucleic acid-enzyme.

DETAILED EXPLANATION OF THE INVENTION

The nucleic acid-enzyme complex of the present invention is composed of the insertion of GGA 12-mer into a catalytic domain of RNA cleavage reaction of the nucleic acid-enzyme.

In the present invention, nucleic acid-enzyme is referred to as ribozyme and deoxyribozyme.

Figure 1:
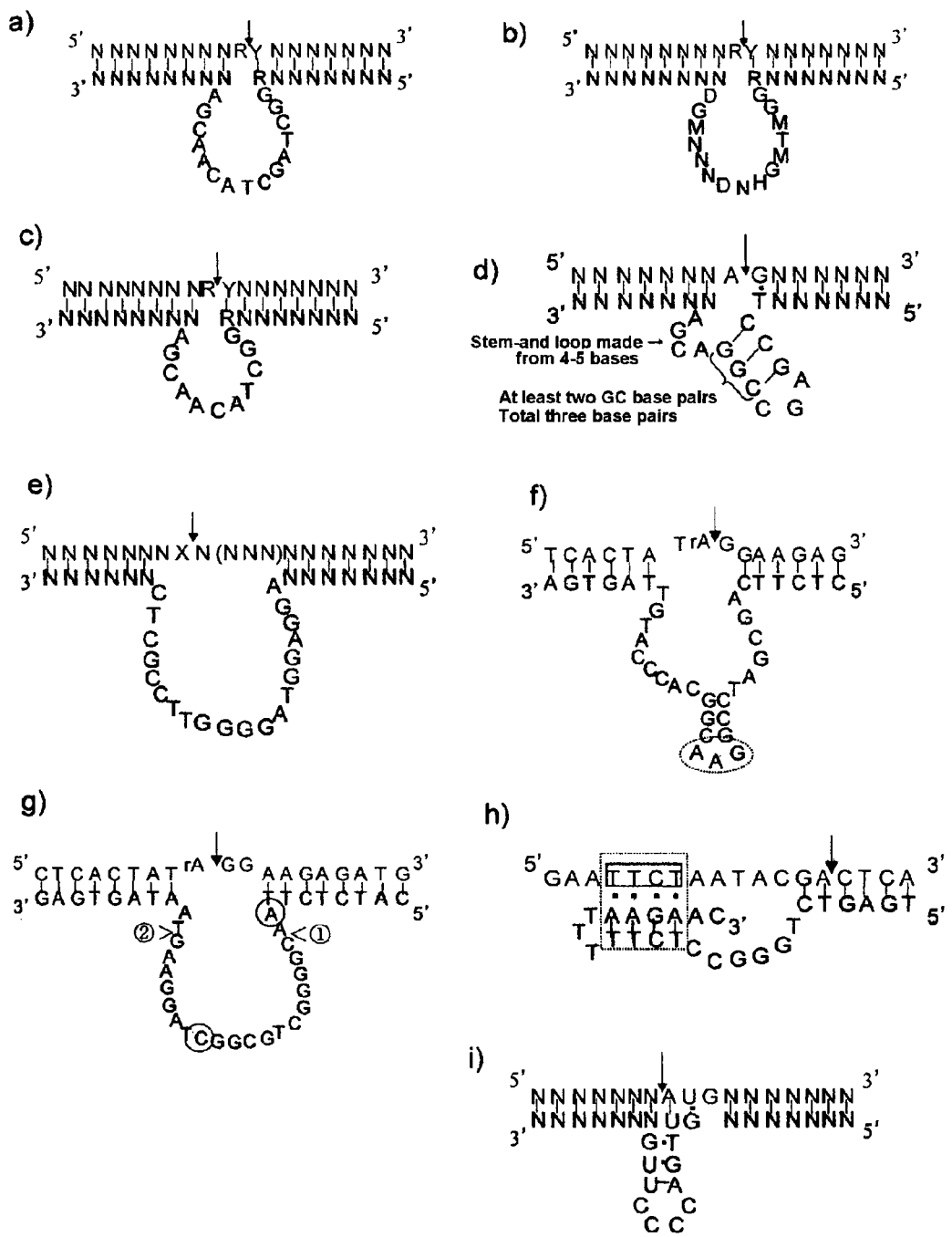
FIG. 1 shows examples of deoxyribozyme usable to the present invention. The arrow heads represent cleavage sites. In a) the upper sequence represents substrate RNA and the lower sequence represents 10-23 deoxyribozyme (5'NNNNNNNRGGCTAGCTACAACGACCCCCCC3' (SEQ ID NO: 5), wherein N represents A, C, G or T; R represents purine bases (G or A); and Y represents pyrimidine bases (C or U)) (Proc. Natl. Acad. Sci. USA 94, 1997, 4262-4266). In b) the upper sequence represents substrate RNA and the lower sequence represents 10-23 deoxyribozyme having a mutated catalytic domain (5'NNNNNNNRGGMT-MGHNDNNNMGDNNNNNNNN3' (SEQ ID NO: 6), wherein M represents A or C; H represents A, C or T; D represents G, A or T) (J. Biol. Chem. 277, 2002, 40617-40622). In c) the upper sequence represents substrate RNA and the lower sequence represents deoxyribozyme, wherein specified consecutive 4 bases of catalytic domain of 10-23 deoxyribozyme are deleted (5'NNNNNNNRGGCTACAAC-GANNNNNNNN3' (SEQ ID NO: 7)) (J. Chem. Soc., Perkin Trans. 2, 1999, 1381-1386). In d) the upper sequence represents substrate RNA and the lower sequence represents 8-17 deoxyribozyme (5'NNNNNNTCCGAGCCGGAC-GANNNNNNN3' (SEQ ID NO: 8)) (Proc. Natl. Acad. Sci. USA 94, 1997, 4262-4266). In e) the upper sequence represents substrate RNA (X represents bases other than G; inside of ( ) could be deleted) and the lower sequence represents Bipartite deoxyribozyme (5'NNNNNNNAGGAGG-TAGGGGTTCCGCTCNNNNNN3' (SEQ ID NO: 9)) (J. Mol. Biol. 313, 2001, 283-294). In f) the upper sequence represents substrate RNA (5'TCACTATAGGAAGAG3' (SEQ ID NO: 22)) and the lower sequence represents E6 deoxyribozyme (5'CTCTTCAGCGATCCGGAACGGCAC-CCATGTTAGTGA3' (SEQ ID NO: 10)). In g) the upper sequence represents substrate RNA (5' CTCACTATAGGAA-GAGATG3' (SEQ ID NO: 23)) and the lower sequence represents HD3 deoxyribozyme (5'CATCTCTTAACGGGGCT-GCGGCTAGGAAGTAATAGTGAG3' (SEQ ID NO: 11)) (Proc. Natl. Acad. Sci. USA 95, 1998, 6027-6031). In h) the upper sequence represents substrate RNA (5'GAAT-TCTAATACGACTCA3' (SEQ ID NO: 24)) and the lower sequence represents a modified deoxyribozyme obtained by the change of class II deoxyribozyme working to cis into that working to trans (5'TGAGTCTGGGCCTCTTTTTAA-GAAC3' (SEQ ID NO: 12)) (Proc. Natl. Acad. Sci. USA 95, 1998, 2233-2237). In i) the upper sequence represents substrate RNA and the lower sequence represents 16.2-11 enzyme (5'NNNNNNNGNTGACCCCNNGNNNNNNN3' (SEQ ID NO: 13) (J. Am. Chem. Soc. 122, 2000, 2433-2439).
Figure 2:
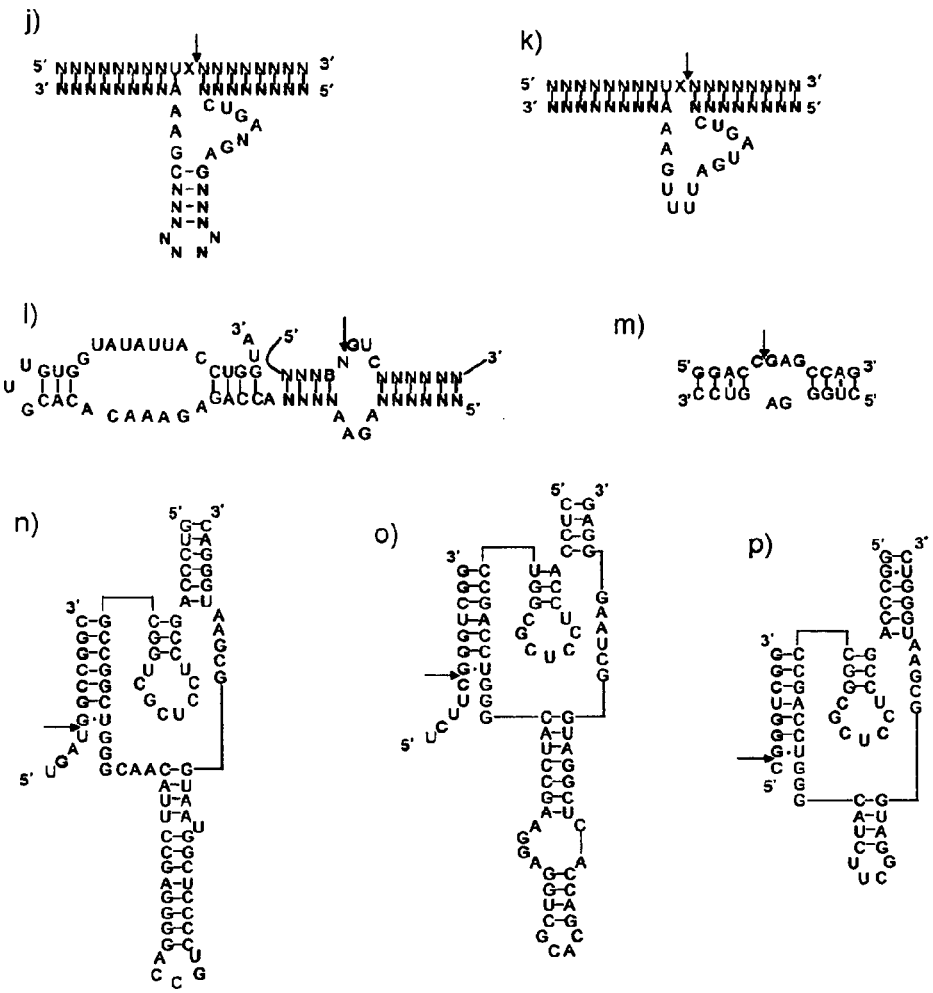
FIG. 2 shows examples of ribozyme usable to the present invention. In j) the upper sequence represents substrate RNA and the lower sequence represents a hammer head type ribozyme (5'NNNNNNNNCUGAN-GAGNNNNNNNNNNCGAAANNNNNNNN3' (SEQ ID NO.: 14) wherein N=A, G, C or U; and X=A, C, or U). In k) the upper sequence represents substrate RNA and the lower sequence represents a miniaturized ribozyme of hammer head type ribozyme (5'NNNNNNNNCUGAUGAUU-UUGAAANNNNNNNN3' (SEQ ID NO: 15), wherein N=A, G, C or U; and X=A, C, or U). In l) the upper sequence represents substrate sequence 5'NNNBNGUCNNNNNN3' (SEQ ID NO: 25) wherein B is G, C, or U, and the lower sequence represents a hairpin type ribozyme (5'NNNNNNA-GAANNNNACCAGAGAAACACACGUUGUG-GUAUAUUACCUGGUA3' (SEQ ID NO: 16) wherein N=A, G, C or U). In m) the upper sequence represents substrate sequence 5'GGACCGAGCCAG3' (SEQ ID NO: 26) and the lower sequence represents lead ribozyme (5'CUGG-GAGUCC3' (SEQ ID NO.: 17) wherein N=A, G, C or U). In n) the substrate sequence is 5'UGAUGGCCGGC3' (SEQ ID NO: 27) and the ribozyme is a HDV ribozyme derived from the genome strand (5'GUCCCAGCCUCCUCGCUGGCGC-CGGCUGGGCAACAUUCCGAGGGGAC-CGUCCCCUCGGUAAUGGCGAAUGGGAC (SEQ ID NO.: 18)). In o) the substrate sequence is 5'UCU-UCGGGUCGG3' (SEQ ID NO: 28) and the ribozyme is a HDV ribozyme derived from the antisense strand (5' CUC-CACCUCCUCGCGGUCCGACCUGGGCAUC-CGAAGGAGGUCGCACGA CCACUCGGAUGGC-UAAGGGAG3' (SEQ ID NO: 19)). In p) the substrate sequence is 5'CGGGUCGG3' (SEQ ID NO: 29) and the ribozyme is a HDV ribozyme variant designed based on n) and o) (5'GGCCCAGCCUCCUCGCGGCCCGAC-CUGGGCAUCUUCGGAUGGCGAAUGGGUC3' (SEQ ID NO.: 20)).

Nucleic acid-enzyme usable in the present invention involves such enzymes as shown in FIG. 1 (deoxyribozyme) and FIG. 2 (ribozyme). Arrow heads in the figures show the cleavage site of target RNA.

a) shows 10-23 deoxyribozyme (SEQ ID NO: 5) (Proc. Natl. Acad. Sci. USA. 94, 1997, 4262-4266) and the details are shown later. The substrate binding domain is bases 1~8 and 24~31 of the sequence and the catalytic domain of RNA cleavage reaction is bases 9~23 of the sequence.

b) shows a mutated catalytic domain of 10-23 deoxyribobozyme (J. Biol. Chem. 277, 2002, 40617-40622) (SEQ ID NO: 6). The substrate binding domain is bases 1~8 and 24~31 of the sequence and the catalytic domain of RNA cleavage reaction is bases 9~23 of the sequence.

c) shows a deoxyribozyme, wherein specified consecutive 4 bases of catalytic domain of 10-23 deoxyribozyme are deleted (J. Chem. Soc., Perkin Trans. 2, 1999, 1381-1386) (SEQ ID NO: 7). The substrate binding domain is bases 1~8 and 20~27 of the sequence and the catalytic domain of RNA cleavage reaction is bases 9~19 of the sequence. The cleavage activity depends on the presence of calcium ion.

d) shows 8-17 deoxyribozyme (Proc. Natl. Acad. Sci. USA. 94, 1997, 4262-4266; J. Biol. Chem. 275, 2000, 11693-11697) (SEQ ID NO: 8). The substrate binding domain is bases 1~7 and 21~27 of the sequence and the catalytic domain of RNA cleavage reaction is bases 8~20 of the sequence.

e) shows Bipartite deoxyribozyme (J. Mol. Biol. 313, 2001, 283-294) (SEQ ID NO: 9). The substrate binding domain is bases 1~7 and 28~33 of the sequence and the catalytic domain of RNA cleavage reaction is bases 8~27 of the sequence.

f) shows E6 deoxyribozyme. This deoxyribozyme has similar second order structure to that of 8~17 deoxyribozyme, but GAA is variable (SEQ ID NO: 10). The substrate binding domain is bases 1~6 and 31~36 of the sequence and the catalytic domain of RNA cleavage reaction is bases 7~30 of the sequence.

g) shows HD3 deoxyribozyme (Proc. Natl. Acad. Sci. USA. 95, 1998, 6027-6031) (SEQ ID NO: 11). The substrate binding domain is bases 1~8 and 32~39 of the sequence and the catalytic domain of RNA cleavage reaction is bases 9~31 of the sequence. HD3 deoxyribozyme is a modification of HD1 or HD2 deoxyribozyme. HD2 deoxyribozyme is obtained by the modification of HD1 by changing Ⓐ to G and Ⓒ to G and by adding T to ① site of HD1, while HD1 deoxyribozyme is obtained by the modification of HD2 by further adding T to ② site of HD2. Histidine is required for cleavage reaction. At a low concentration of histidine, the cleavage activity decreases in the order HD3, HD2, HD1.

h) shows a modified deoxyribozyme obtained by the change of class II deoxyribozyme working to cis into that working to trans (Proc. Natl. Acad. Sci. USA. 95, 1998, 2233-2237) (SEQ ID NO: 12). The substrate binding domain is bases 1~6, 13~16 and 20~23 of the sequence and the catalytic domain of RNA cleavage reaction is bases 7~18 of the sequence. TTCT represents poly-pyrimidine region and could be changed by a sequence rich in pyrimidine (ex. CTTT). Noteworthily, the region enclosed by a dotted square shows triple-helix interactions.

i) shows 16.2-11 enzyme (J. Am. Chem. Soc. 122, 2000, 2433-2439) (SEQ ID NO: 13).
The substrate binding domain is bases 1~9 and 20~26 of the sequence and the catalytic domain of RNA cleavage reaction is bases 10~19 of the sequence.

j) shows hammer head type ribozyme (SEQ ID NO: 14). The substrate binding domain is bases 1~8 and 31~39 of the sequence and the catalytic domain of RNA cleavage reaction is bases 9~30 of the sequence.

k) shows miniaturized ribozyme of hammer head type ribozyme (SEQ ID NO: 15). The substrate binding domain is bases 1~8 and 23~31 of the sequence and the catalytic domain of RNA cleavage reaction is bases 9~30 of the sequence.

l) shows hairpin type ribozyme (SEQ ID NO: 16). The substrate binding domain is bases 1~6 and 12~14 of the sequence and the catalytic domain of RNA cleavage reaction is bases 15~50 of the sequence.

m) shows lead ribozyme (SEQ ID NO: 17). The substrate binding domain is bases 1~4 and 7~10 of the sequence and the catalytic domain of RNA cleavage reaction is bases 4~7 of the sequence.

n) shows HDV ribozyme (derived from genome strand) (SEQ ID NO: 18). The substrate binding domain is bases 21~27 of the sequence and the catalytic domain of RNA cleavage reaction is bases 1~20 and 28~74 of the sequence.

o) shows HDV ribozyme (derived from antisense strand) (SEQ ID NO: 19). The substrate binding domain is bases 18~24 of the sequence and the catalytic domain of RNA cleavage reaction is bases 1~17 and 25~69 of the sequence.

p) shows HDV ribozyme variant designed based on n) and o) (SEQ ID NO: 20). The substrate binding domain is bases 20~26 of the sequence and the catalytic domain of RNA cleavage reaction is bases 1~19 and 27~52 of the sequence.

Additionally, a sequence accompanying linker at least at one end, preferably at both ends of GGA 12-mer instead of GGA 12-mer could be used. The linker involves oligonucleotide comprising about 1~4 nucleotides, divalent hydrocarbon group comprising about 2~10 carbons, and peptide comprising about 1~4 amino acids. The oligonucleotide could be random sequence. The hydrocarbon is preferably exhibited as —$(CH_2CH_2)n$- (n=about 1~5). The peptide comprises preferably amino acids of simple structure as glycine.

Figure 3:
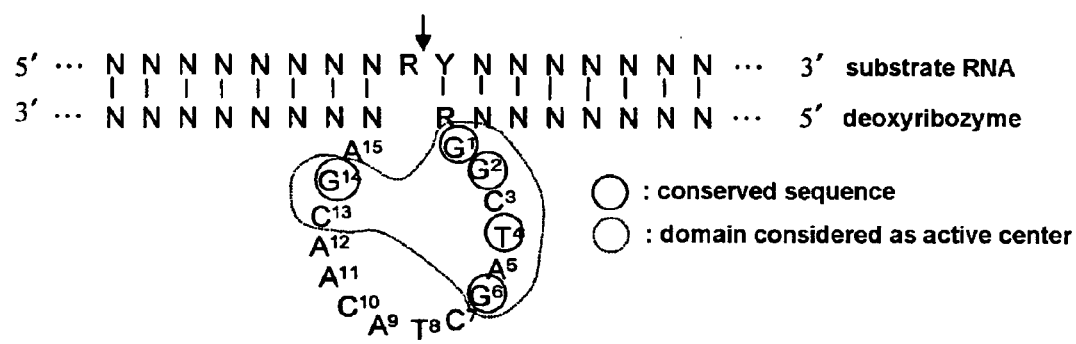
FIG. 3 shows 10-23 type deoxyribozyme (5'TCTTTC-CAGGCTAGCTACAACGAATTGAATA3' (SEQ ID NO.: 4)) used in the example. N represents A, C, G or T (or U); Y represents U or C; R represents A or G.

FIG. 3 shows 10-23 type deoxyribozyme (SEQ ID NO: 4) as a preferable example of nucleic acid-enzyme. The substrate binding domain is bases 1~8 and 24~31 of the sequence and the catalytic domain of RNA cleavage reaction is bases 9~23 of the sequence. The enzyme derived from $23^{rd}$ clone obtained after 10 times selection of in vitro selection method (Proc. Natl. Acad. Sci. USA (1997) 94, 4262-4266). The reaction rate of the enzyme is higher than that of endoribonuclease for nucleic acids and proteins. It is suggested from kinetic aspect that the catalytic mechanism of 10-23 type deoxyribozyme is similar to that of hammer head ribozyme (Biochemistry 37, 13330-13342, 1998). The sequence of catalytic domain of RNA cleavage reaction composed of 15 residues is highly conserved and the residues, surrounded by O as shown in FIG. 3, are particularly highly conserved. It is considered that the domain surrounded by a dotted line is directly related to the formation of catalytic domain of RNA cleavage reaction (J. Biol. Chem. 277, 40617-40622, 2002).

The nucleic acid-enzyme used in the present invention comprises a catalytic domain of RNA cleavage reaction and substrate binding domains, and preferably comprises a catalytic domain of RNA cleavage reaction, which is edged with two substrate binding domains complementary to target RNA.

The substrate binding domains in a nucleic acid-enzyme complex could be freely modified to be complementary to target RNA. In this way, desired RNA could be targeted. The base numbers of substrate binding domain are preferably independently 8±4, more preferably 8±2.

Furthermore, a target RNA is preferably exhibited as ARB (in the formula, A and B represent the binding domains, the nucleotide residue of B proximal to R represents uridine or cytidine and R represents adenosine or guanosine).

On the other side, the catalytic domain of RNA cleavage reaction, wherein GGA 12-mer is inserted, is determined by original nucleic acid-enzyme. "Essential elements for the activity of nucleic acid-enzyme, from which nucleic acid-enzyme complex is originated" are $Mg^{2+}$, $Ca^{2+}$, $Mn^{2+}$, $Pb^{2+}$, $Cd^{2+}$, $Sr^{2+}$, $Ba^{2+}$ et al. These ions should be present in the medium at 1~500 mM.

Figure 4:
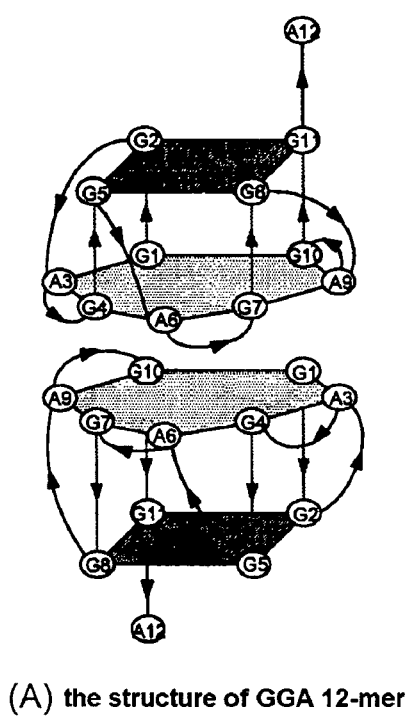
FIG. 4 shows schematically the structure of GGA12-mer in the presence of monovalent metal ion. (A) shows the whole structure of the homodimer of GGA 12-mer (5'GGAGGAG-GAGGA3' (SEQ ID NO: 21)), (B) shows G:G:G:G tetrad, and (C) shows G(:A):G(:A):G(:A):G heptad.
Figure 4:
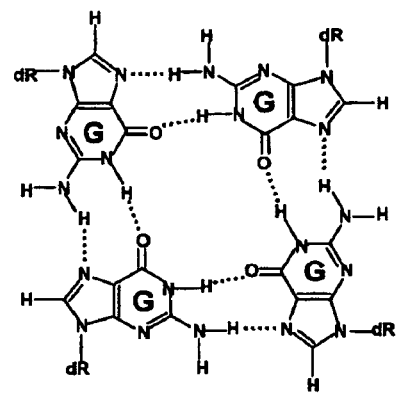
Figure 4:
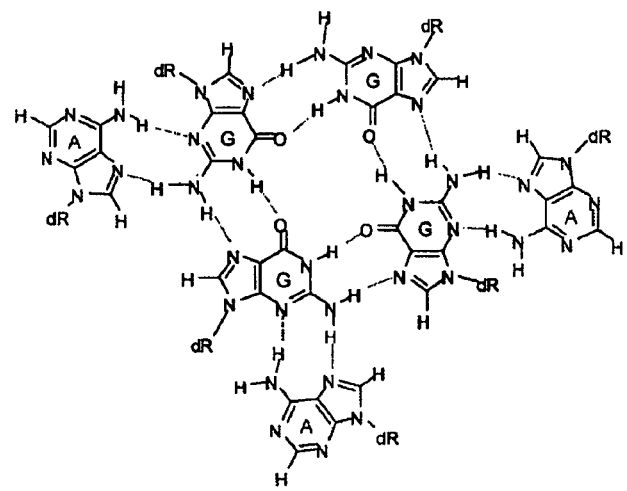

The sequence d(GGAGGAGGAGGA) (SEQ ID NO: 21; GGA 12-mer) is inserted into the catalytic domain of RNA cleavage reaction. FIG. 4 (A) shows schematically the structure of GGA 12-mer. As a whole, the structure is a homodimer with the association of two molecules of GGA 12-mer. Individual monomer formed a structure linked by hydrogen bonds (G:G:G:G tetrad, FIG. 4 (B)) based on four guanine residues, i.e. G2, G5, G8 and G11, located on the same plane, and a structure linked by hydrogen bonds (G(:A):G(:A):G(:A):G heptad, FIG. 4 (*c*)) based on total 7 bases composed of four guanine bases, i.e. G1, G4, G7 and G10, and three adenine bases, i.e. A3, A6 and A9, located on the same plane. DNA rich in G bases forms not only quadruplex chain structure but also tetrad under physiological condition in vitro. Moreover, heptad is formed by the use of tetrad as a core structure and by allocation of three adenines around the core by G:A base pairs, referred to as sheared type. In a monomer, structure of tetrad and heptad are stabilized by stacking interaction between them. Also, A12 at the end is stacking with G11 in the tetrad (FIG. 4 (A)).

The nucleic acid forming quadruplex chain structure shows an extended structure with single strand in the absence of monovalent metal ion such as K+, but shows quadruplex chain structure by the addition of necessary concentration of monovalent metal ions (FIG. 4 (A)).

Figure 5:
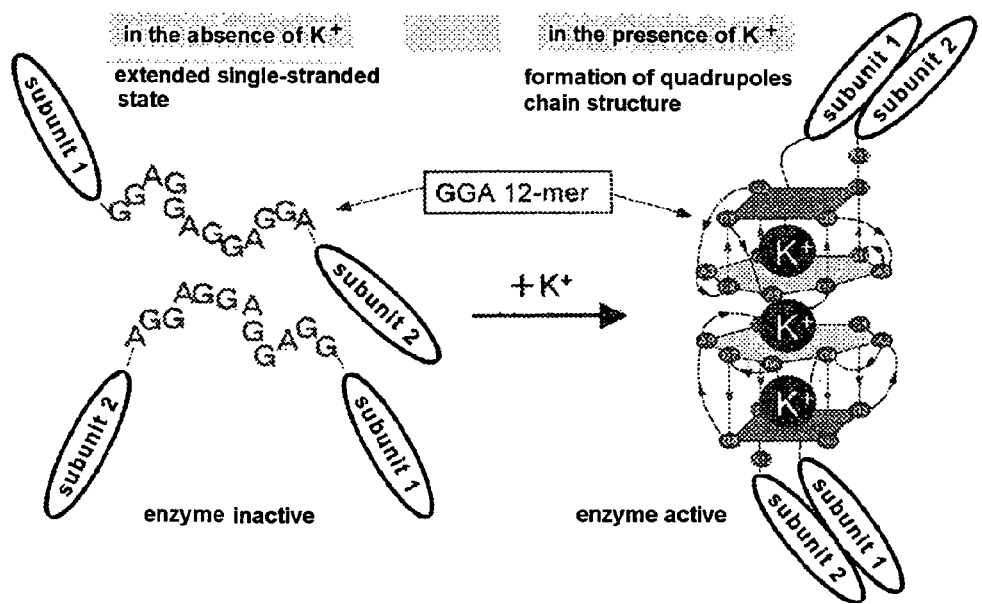
FIG. 5 shows a schematic picture (left side) of the binding between deoxyribozyme and GGA 12-mer (5'GGAGGAG-GAGGA3' (SEQ ID NO: 21)) and a picture (right side), in which presence of potassium ion changes GGA 12-mer to quadruplex chain structure and allows two separated subunits to come close each other.

The two subunit of nucleic acid-enzyme separated at the catalytic domain of RNA cleavage reaction is bound by keeping G1 and A12 of each GGA 12-mer to 5'→3' direction. The bound state is shown in FIG. 5.

The nucleic acid-enzyme complex prepared as above described is used normally in the presence of such medium as phosphate buffer (50 mM, pH 7.9), $Mg^{2+}$ (25 mM) et al. Changing the concentration of monovalent metal ion in the medium could allow structural change of the GGA 12-mer to control the switching ON/OFF or the degree of RNA cleavage activity of the nucleic acid-enzyme (FIG. 5).

The above monovalent metal ions involve $K^+$, $Na^+$ et al. The quadruplex chain structure is more stable in the presence of $K^+$ than $Na^+$.

In the presence of the monovalent metal ion at less than 10 mmol/L, preferably at less than 5 mmol/L, most preferably at 0 mmol/L, GGA 12-mer has extended structure of single strand, and RNA cleavage activity of nucleic acid-enzyme is switched off or becomes weak.

In contrast, in the presence of the monovalent metal ion at more than 10 mmol/L, preferably at more than 30 mmol/L, most preferably at more than 30~200 mmol/L, GGA 12-mer has a quadruples chain structure and two subunits of nucleic acid-enzyme has functional configuration, which allow RNA cleavage activity to be switched on or to be strong.

There is substantial difference of potassium ion between intracellular and extracellular concentration, i.e. while intracellular concentration is around 140 mM, extracellular concentration is around 5 mM. Since the differential concentration of potassium ion could control the switching or the degree of the cleavage activity, the nucleic acid-enzyme complex of the present invention could be applied to various fields.

It is possible to repress the extracellular activity (low concentration of monovalent potassium ion) and to recover the intracellular activity (high concentration of monovalent potassium ion) allowing to inhibit the expression of pathogenic proteins by introducing the nucleic acid-enzyme complex of the present invention into cells. It is unlikely for the nucleic acid-enzyme complex of the present invention to injure human body by extracellular enzyme activity under normal condition.

For example, the nucleic acid-enzyme complex of the present invention could intracellularly cleave and inactivate mRNA of pathogenic gene derived from such virus as HIV virus and influenza virus, which induce disease, and mRNA of cancer gene.

The method for introducing the nucleic acid-enzyme complex of the present invention into cells involve the following procedures:
1) Methods for introducing the nucleic acid-enzyme complex of the present invention into specific cells:
A) Isolating the cell out of a living organism, introducing the nucleic acid-enzyme complex into the cell by gene guns and setting back the cells into the living organism.
B) Isolating the cell out of a living organism, introducing the nucleic acid-enzyme complex into the cell by electroporation and setting back the cells into the living organism. These methods are useful for marrow cells.
2) Methods for introducing the nucleic acid-enzyme complex of the present invention into nonspecific cells:

It is possible to introduce effectively deoxyribozyme complex into cells by binding the nucleic acid-enzyme complex with a cationic lipid to form a liposome-nucleic acid-complex and making the liposome-nucleic acid-complex contact with the cell, which results in fusing the complex with cell membranes.

The following examples are shown to further illustrate the present invention, but it is not intended to limit the scope of the present invention. The following examples used 10-23 type deoxyribozyme as a nucleic acid-enzyme.

Preparative Example 1

A domain of mRNA containing initiation codon AUG of PB2, a subunit of RNA polymerase of influenza virus (SEQ ID NO: 2) (FEBS Lett. 481, 113-116, (2000)) was synthesized by DNA/RNA synthesizer by a phosphoramidite method as a target (substrate RNA). During the procedures, fluorescent dye (Cy-5) was introduced to the 5' end base.

Example 1

Figure 6:
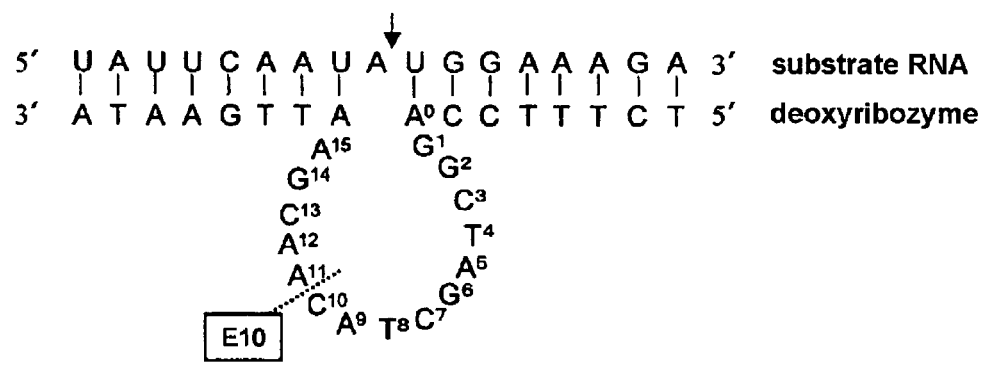
FIG. 6 shows the insertion site (E10) of GGA 12-mer into 10-23 type deoxyribozyme (5'TCTTTCCAGGCTAGCTA-CAACGAATTGAATA3' (SEQ ID NO.: 4)) to form "GGA12E10". The substrate sequence is 5'UAUU-CAAUAUGGAAAGA3' (SEQ ID NO: 2).

Two subunits obtained by cleavage at E10 (cf. FIG. 6) of 10-23 type deoxyribozyme were connected to GGA 12-mer to prepare the complex "hereinafter referred to as GGA12E10" (SEQ ID NO: 3).

10 pM GGA12E10, 0 or 100 mM KCl and 50 mM buffer were mixed in 10 μl reaction volume, heated at 95° C. for 5 min and annealed by cooling slowly.

Then, substrate RNA obtained in the preparative example 1 was added to final 1 μM and the reactant was incubated at 37° C. for 30 min. After that, $MgCl_2$ was added to final 25 mM to start the reaction. The reaction was performed at 37° C. At 0, 24, 48, 96 and 168 hr after the start, a portion of the solution was collected, stopped the reaction by the addition of sufficient volume of stopping solution and stored in a refrigerator. After all of the reaction were stopped, samples were electrophoresed on 20% denatured polyacrylamide gel at 15 mA of constant current, RNA with Cy5 labeled 5' end was detected by Bioimaging-analyzer (FLA-2000, Fujifilm LTD) and the cleavage activity was measured. pH was 7.9 (phosphate buffer).

Figure 7:
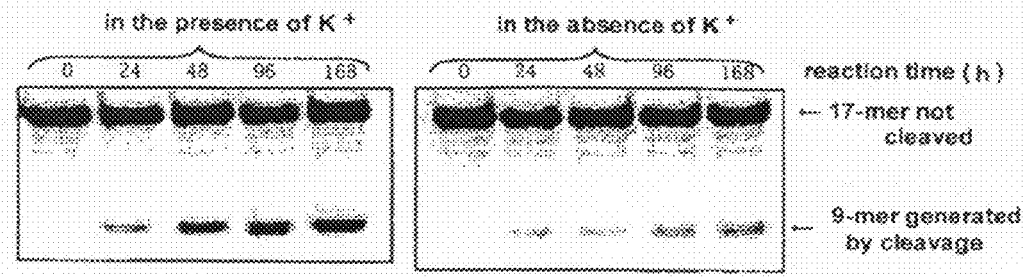
FIG. 7 shows a result of electrophoresis exhibiting different cleavage activity in "GGA12E10" in the presence or absence of potassium ion (Example 1).

FIG. 7 shows the result. The cleavage fraction at 168 hr was 12.2% in the presence and 3.5% in the absence of potassium ion. Addition of potassium ion might lead quadruplex chain structure, which allows two subunits to come close each other, to reconstitute the active structure of catalytic domain of deoxyribozyme and to enhance the cleavage activity.

Example 2

Figure 8:
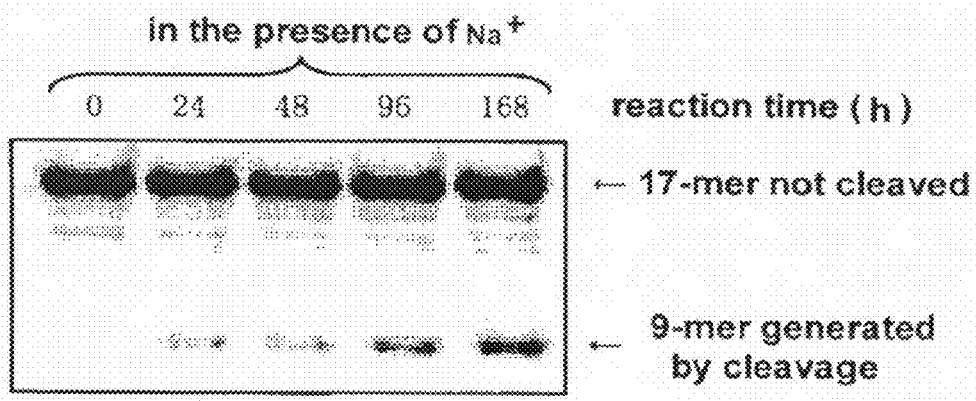
FIG. 8 shows a result of electrophoresis exhibiting different cleavage activity in "GGA12EI0" in the presence or absence of sodium ion (Example 2).

The same procedure as example 1 was performed by the use of NaCl instead of KCl. FIG. 8 shows the result. The cleavage activity was observed also in the presence of Na$^+$. However, the cleavage fraction was higher in the presence of potassium ion than in that of sodium ion.

Comparing FIG. 7 with FIG. 8 quantitatively, it was found that the cleavage fraction at 168 hr in the presence of potassium ion was 12.2% and that in the presence of sodium ion was 5.5%. As described previously, it is interpreted as that the quadruplex chain structure formed by GGA 12-mer is stabilized in the presence of potassium ion more than that of sodium ion and the cleavage activity of the deoxyribozyme was enhanced.

Comparative Example 1

The same procedure as example 1 was performed by the use of wild type 10-23 deoxyribozyme (SEQ ID NO: 4) instead of GGA12E10. pH was 8.0 (Tris-HCl).

Figure 9:
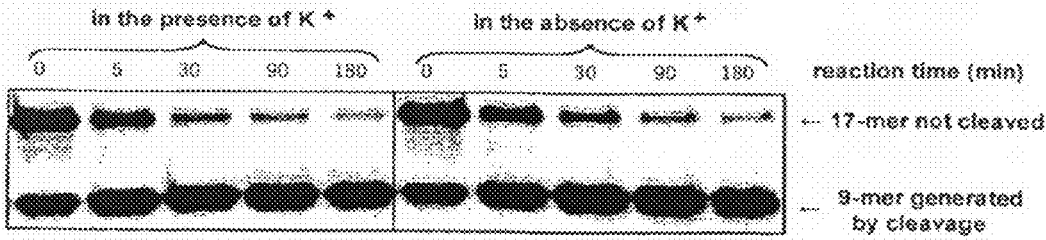
FIG. 9 shows a result of electrophoresis exhibiting the cleavage activity in wild type 10-23 deoxyribozyme (comparative example 1).

FIG. 9 shows the result. The wild type has cleavage activity regardless of the presence of potassium ion. The difference of the cleavage activity at each reaction time between in the presence and in the absence of potassium ion was less than 1%.

What is claimed is:

1. A nucleic acid-enzyme complex comprising a catalytic domain of RNA cleavage reaction and a substrate binding domain of a nucleic acid-enzyme and a sequence (5'GGAG-GAGGAGGN3') (SEQ ID NO: 1), wherein the substrate binding domain has a complementary relationship to the binding site of a target RNA and the sequence (5'GGAG-GAGGAGGN3') (SEQ ID NO: 1) or a sequence having a linker at least to one of both ends of the sequence is inserted in the catalytic domain of the RNA cleavage reaction.

2. The nucleic acid-enzyme complex of claim 1, wherein the nucleic acid-enzyme is ribozyme or deoxyribozyme.

3. The nucleic acid-enzyme complex of claim 1, wherein the nucleic acid-enzyme complex has two substrate binding domains and the catalytic domain of RNA cleavage reaction is sandwiched by the two substrate binding domains.

4. The nucleic acid-enzyme complex of claim 1, wherein the substrate binding domains have independently 8±4 bases.

5. The nucleic acid-enzyme complex of claim 4, wherein the nucleic acid-enzyme is 10-23 deoxyribozyme and the target RNA is represented by a formula ARB, wherein A and B represent the binding domains, the nucleotide residue of B proximal to R represents uridine or cytidine and R represents adenosine or guanosine.

6. A method for controlling target RNA cleavage in a system comprising the nucleic acid-enzyme complex of claim 1, an element essential for making the nucleic-acid enzyme active, a target RNA and a monovalent metal ion, wherein the nucleic-acid enzyme is the origin of the nucleic acid-enzyme complex, comprising the steps of keeping the concentration of the monovalent metal ion at more than or equal to 10 mmol/L and keeping the concentration of the monovalent metal ion at less than 10 mmol/L.

7. The method of claim 6, wherein the monovalent metal ion is potassium ion.

8. The method for cleaving an target RNA located in a cell comprising introducing the nucleic acid-enzyme complex of claim 1 into the cell by any one of the following procedures:
   (A) Isolating the cell out of a living organism and introducing the nucleic acid-enzyme complex into the cell by gene guns or by electroporation; and
   (B) Binding the nucleic acid-enzyme complex with a cationic lipid to form a liposome-nucleic acid-complex and making the liposome-nucleic acid-complex contact with the cell.

9. A cell comprising the nucleic acid-enzyme complex of claim 1.

* * * * *